United States Patent [19]

Brooks et al.

[11] Patent Number: 5,513,537
[45] Date of Patent: May 7, 1996

[54] METHOD AND APPARATUS TO DETERMINE COMPOSITE PREPREG TACK

[75] Inventors: John R. Brooks; Philip R. Platt, both of Sumner, Wash.

[73] Assignee: The Boeing Company, Seattle, Wash.

[21] Appl. No.: 440,786

[22] Filed: May 15, 1995

Related U.S. Application Data

[63] Continuation of Ser. No. 144,701, Oct. 28, 1993, abandoned, which is a continuation-in-part of Ser. No. 840,882, Feb. 25, 1992, abandoned.

[51] Int. Cl.⁶ .................................................. G01B 11/28
[52] U.S. Cl. .................................................. 73/865.8
[58] Field of Search .................................. 73/865.8, 827, 73/834, 835, 150 A; 356/379, 380; 156/378; 348/135, 137

[56] References Cited

U.S. PATENT DOCUMENTS

| | | | |
|---|---|---|---|
| 2,775,888 | 1/1957 | Pickup | 73/150 |
| 2,834,205 | 5/1958 | Pickup | 73/150 |
| 2,982,129 | 5/1961 | Wetzel et al. | 73/150 |
| 3,067,646 | 12/1962 | Reesen | 73/150 A |
| 3,186,221 | 6/1965 | Steib | 73/150 |
| 3,214,971 | 11/1965 | Hammond, Jr. | 73/150 |
| 3,253,461 | 5/1966 | Blanchard et al. | 73/150 A |
| 3,396,578 | 8/1968 | Skundberg | 73/150 |
| 3,444,732 | 5/1969 | Robbins et al. | 73/150 |
| 3,741,012 | 6/1973 | Day | 73/150 A |
| 4,312,212 | 1/1982 | Clendenin | 73/15.4 |
| 4,637,252 | 1/1987 | Rhee et al. | 73/150 A |
| 4,800,287 | 1/1989 | Green, Sr. et al. | 356/380 |
| 4,856,325 | 8/1989 | Tomita et al. | 73/150 A |
| 4,888,985 | 12/1989 | Siemer | 73/150 A |
| 4,893,503 | 1/1990 | Kimura et al. | 73/150 A |
| 5,207,889 | 5/1993 | Wolski et al. | 205/155 |
| 5,275,489 | 1/1994 | Borneman et al. | 73/150 A |

FOREIGN PATENT DOCUMENTS

| | | |
|---|---|---|
| 4211866A1 | 10/1992 | Germany . |
| 0116204 | 5/1987 | Japan ................................ 356/379 |
| 404191641A | 7/1992 | Japan . |
| 1467457A1 | 3/1989 | U.S.S.R. . |

*Primary Examiner*—Robert Raevis
*Attorney, Agent, or Firm*—Christensen O'Connor Johnson & Kindness

[57] ABSTRACT

A method and apparatus for determining whether the tack of a composite prepreg is within an appropriate range to adhere to a substrate when joined under predetermined conditions. The resulting tack measurement can be used as a measurement of quality control for prepreg's used in automated tape-laying machines, hand layup operations, or as a control variable in prepreg development. An embodiment of an apparatus of the present invention has the ability to simulate the prepreg layup of an automated tape-laying machine. This includes the ability to adjust the rate at which the prepreg is laid up, the force used layup the prepreg, the durometer of the material from which the application roller is formed, and the diameter of the application roller used to layup the prepreg. One embodiment of the apparatus includes a table with a movable platform capable of joining two strips of prepreg under conditions similar to an automated tape-laying machine by moving the prepreg between the platform and the application roller. The table is connected to a controller that adjusts the rate at which the prepreg is moved into contact with the application roller. The joined strips of prepreg are then separated and a value of tack, such as the average force or energy required to separate the strips is measured. In another embodiment of the present invention, contrast analysis is used to determine the adhesive contact area between a strip of prepreg and a visually transparent substrate. The percent adhesive contact area is then used as a measurement of prepreg tack.

7 Claims, 8 Drawing Sheets

METHOD AND APPARATUS TO DETERMINE COMPOSITE PREPREG TACK

This application is a continuation application based on prior application Ser. No. 08/144,701, filed on Oct. 28, 1993, now abandoned which is a continuation-in-part of application Ser. No. 07/840,882, filed Feb. 25, 1992, now abandoned.

FIELD OF THE INVENTION

The present invention relates to methods and apparatus for measuring the tack of composite prepreg, specifically, to techniques for determining whether the tack of the prepreg is within an acceptable range to join a strip of prepreg to an underlying substrate.

BACKGROUND OF THE INVENTION

Composite materials are widely used in the fabrication of products ranging from tennis racquets to advanced aerospace structures. One type of composite material used in aerospace structures is available in the form of a sheet consisting of continuous parallel reinforcing fibers embedded within an organic matrix material. Typically, the matrix material is an adhesive system such as an epoxy resin. The sheet consisting of reinforcing fibers and matrix material is known as "prepreg."

Prepreg is commonly provided from a manufacturer as a continuous sheet wound on a roll or spool, with the fibers extending longitudinally around the spool. The prepreg can be purchased in widths ranging from centimeters to meters. Typically, the wider prepreg spools are used in hand layup procedures in which individual layers or plies of prepreg are manually placed on top of each other by a worker. The narrower spools or tapes are typically used in automated tape-laying machines or winding machines.

Automated tape-laying machines use a continuous spool of composite prepreg and a robotic arm to apply individual plies of prepreg to a pan or substrate in the desired fiber orientations. The tape-laying machines are capable of starting an individual ply at the location desired, laying up the ply over the distance desired, and then ending or cutting the ply at the location desired. Many tape-laying machines use a robotic arm that terminates with a round application roller. As the robotic arm moves, the roller brings the prepreg into contact with the part and places a force on the prepreg in the direction of the surface of the part. The force causes the prepreg to adhere to the underlying substrate or part. As the robotic arm moves forward, the tack of the prepreg maintains the individual plies in position. If the tack of the prepreg is insufficient, the prepreg does not adhere to the underlying substrate.

The tape-laying machine's ability to properly place the prepreg tape, and thus the resulting part quality, is greatly influenced by the stickiness or tack of the prepreg used on the machine. Prepreg tape that has insufficient tack can result in the prepreg shifting during layup or lifting or sliding out of the proper position after being laid up. This undesirable movement can prevent fabrication of the part altogether, require additional manual adjustment, or can result in parts that have voids or gaps between individual prepreg tapes or which are not within the desired dimensional or structural tolerances. Similarly, prepreg with too high a degree of tack can also cause improper placement of the prepreg tape or can prevent repositioning of the prepreg after improper placement.

In order to work properly in a tape-laying machine, the prepreg must have the proper tack to prevent shifting, lifting, or sliding of the laid-down prepreg over the typical laydown rate profile of the tape-laying machine. Tape-laying machines generally begin a laydown pass with the application roller stopped and in contact with the composite part. The tape-laying machine then accelerates to a predetermined laydown speed, which it maintains over the majority of each laydown pass. The tape-laying machine then decelerates near the end of each laydown pass in order to increase compaction, and thus prepreg adherence, prior to cutting the prepreg and completing the laydown pass.

To work properly, the laid down prepreg must adhere to the underlying substrate during the acceleration portion of the laydown pass, during the constant-speed portion of the laydown pass and during the deceleration portion and subsequent cut-off portion of the laydown pass. Failure of the prepreg to remain adhered during any part of the laydown pass could create flaws in the final part or require the prepreg to be manually compacted in areas where the prepreg did not adhere properly.

A number of variables influence the tack of the prepreg and its adherence to an underlying substrate. Such variables include the matrix material used in the prepreg, the temperature and humidity at which the prepreg is laid up, the rate at which the prepreg is laid up, the force used to place the prepreg, the age of the prepreg, the durometer of the material that forms the application roller, the diameter of the application roller, and the amount of tithe the prepreg has been exposed to the air prior to use. A number of these variables are directly influenced by the material properties of the prepreg itself, and can differ with each batch of prepreg received from the manufacturer. Each batch of prepreg often has a different value of tack, due to minor changes in the reinforcing fibers, matrix, or prepregging procedures.

A limited range of tack differences can be accounted for by adjusting the tape-laying machine, in order to control the force used to layup the prepreg, the rate at which the prepreg is laid up, the durometer of the material from which the application roller is formed, and diameter of the application roller. Adjusting the diameter and the durometer of the material from which the roller is formed changes the way the force is applied to the prepreg, thus influencing the prepreg's adherence to a substrate. However, if the tack of the prepreg is not within a suitable range, adjusting the tape-laying machine cannot compensate for the poor quality prepreg. Therefore, prepreg that has an improper amount of tack should be rejected upon receiving the prepreg from the manufacturer.

In the past, there has not been a standardized procedure to monitor the tack of composite prepreg prior to using the prepreg in a tape-laying machine. Therefore, there has been no standard measurement available that could be used as a quality control variable in accepting or rejecting different batches of prepreg. In the past, each roll of prepreg would be placed in the tape-laying machine before it could be determined whether or not the prepreg was acceptable. This resulted in a loss of time and money in setting up the tape-laying machine and performing trial runs prior to determining whether the prepreg was acceptable.

SUMMARY OF THE INVENTION

The present invention provides a method and apparatus for determining whether a composite prepreg's tack is within an acceptable range to adhere to a substrate when joined under predetermined conditions. The resulting tack measurement can be used as a measurement of quality control for prepreg's used in automated tape-laying machines, hand layup operations, or as a control variable in prepreg development. This allows a manufacturer to test each batch of prepreg prior to using the prepreg in a manufacturing operation. Therefore, each batch of prepreg can be accepted or rejected based upon its value of tack prior to expending time or money in trial runs using the prepreg. The measurement of tack can also be used during prepreg development to measure the effect of changes in the prepregging manufacturing process on prepreg tack and to optimize layup and handling performance. The measurement of tack can also be used to determine whether the prepreg has sufficient tack to adhere to a release coated tool.

The present invention allows the tack of the prepreg to be determined under conditions similar to those used in the manufacturing environment of a tape-laying machine. This ensures that the measured value of tack is relevant to the specific application in which the prepreg is to be used. One embodiment of the present invention has the ability to vary the rate at which the prepreg is laid up, the force used to layup the prepreg, the durometer of the material used to form the application roller, and the application roller's diameter. The present invention can be used not only in quality control, but also to determine the settings which should be used on a tape-laying machine to get the optimum adhesion, including the optimum rates and forces for laying up the prepreg.

In one embodiment of the present invention, strips from a first batch of prepreg are joined under predetermined conditions. The strips are then separated, and the separation force is measured and converted into a value of tack. Strips from a second batch of prepreg are then joined under the predetermined conditions and a second value of tack is determined. The second value of tack is then compared to the first value of tack to determine whether the second batch of prepreg has an appropriate range of tack to adhere to the substrate.

One embodiment of an apparatus for joining composite prepreg according to the present invention comprises a base and a rotatable roller coupled to the base. The apparatus also includes platform means for mounting a strip of prepreg such that the strip of prepreg is moved into contact with the roller. The roller applies a force to the strip of prepreg in order to join the strip to a substrate under conditions similar to an automated tape-laying machine. Control means for controlling the rate at which the platform means moves the strip of prepreg into contact with the roller is also provided.

According to other aspects of the invention, rate means for varying the rate at which the platform means moves the strip of prepreg into contact with the roller over the length of the strip is provided. Furthermore, the control means also comprises storage means and selection means for storing and selecting more than one rate profile for joining the strip of prepreg to the substrate. The apparatus also includes an arm pivotally coupled to the base in which the roller is rotatably mounted. Applying a force to one end of the arm with an expandable actuator forces the roller against the platform means. Means for adjusting the distance between the roller and the platform means such that a tool can be placed between the roller and platform means is also included. After joining the strip of prepreg to the substrate, the strip is separated from the substrate at an established rate. The force used to separate the strips is measured and converted into a value of tack. The tack is measured as a value of force per unit width or as a value of energy.

In another embodiment of the present invention, the tack of a composite prepreg is determined as a measurement of percent adhesive contact area between the strip of prepreg and a substrate that is at least partially visually transparent. A measurement of percent adhesive contact area for a first and second batch of prepreg is determined. The measurements of percent adhesive contact area are then compared to determine whether or not the tack of the second batch of prepreg is within an appropriate range.

According to other aspects of the invention, an image of the adhesive contact area between the strip of prepreg and the substrate is produced. The area of the image having a contrast greater than a threshold contrast value is then determined. A measurement of percent adhesive contact area between the strip of prepreg and the substrate is then determined using the area of the image having a contrast value greater than the threshold contrast value. The area of the image is determined by counting the number of pixels in the image having a contrast greater than the threshold contrast value. The threshold contrast value may be the value of contrast at a pixel count that is one-half a maximum pixel count or could be the value of contrast at lowest value of pixel count between two peak values of pixel count.

BRIEF DESCRIPTION OF THE DRAWINGS

The foregoing aspects and many of the attendant advantages of this invention will be more readily appreciated as the same becomes better understood by reference to the following detailed description, when taken in conjunction with the accompanying drawings, wherein.

DETAILED DESCRIPTION OF THE PREFERRED EMBODIMENT

Figure 1:
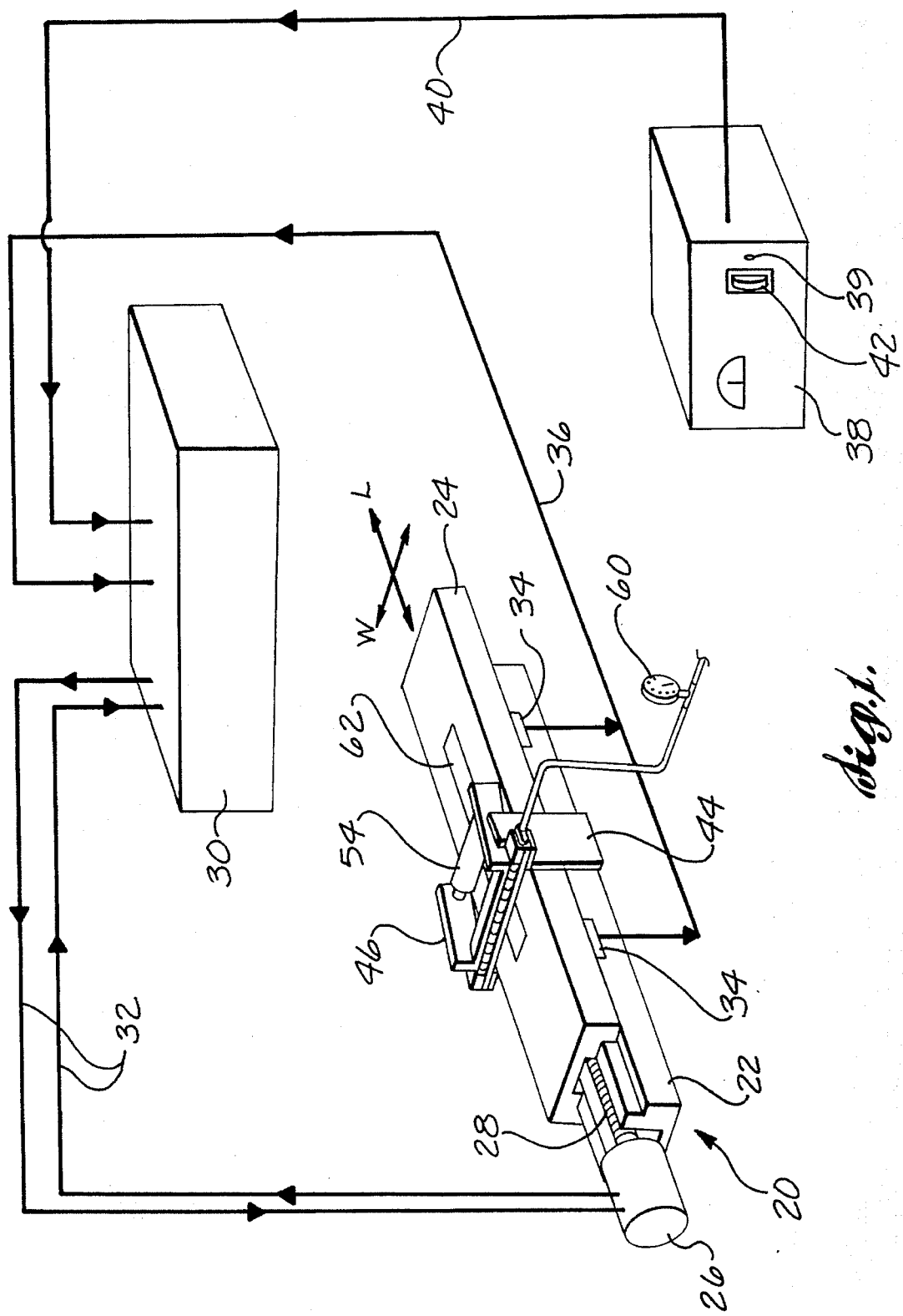
FIG. 1 is a perspective view of a preferred embodiment of an apparatus for joining composite prepreg materials for tack testing.

Referring initially to FIG. 1, a preferred embodiment of an apparatus for determining the tack of a composite prepreg comprises a table 20, a controller 30 and a selection circuit 38. The table includes a fixed base 22 and a movable platform 24. The platform is driven longitudinally (L) with respect to the base through the use of a motor 26 that drives a spindle 28, that in turn, drives the platform. The table is sized such that its width (W) is sufficient to receive typical widths of composite prepreg tape. In one exemplary embodiment, the table is ten inches wide and the platform is capable of 22 inches of travel with respect to the base.

The motor 26 is connected to a controller 30 through the use of a feedback loop as illustrated by lines 32. The controller produces a signal that passes through the feedback loop and adjusts the rate at which the motor 26 drives the platform 24. The controller has the ability to store a series of movement profiles on programmable EPROMs (not shown) contained within the controller 30. These movement profiles contain information which allows the controller to vary the rate at which the platform 24 moves longitudinally with respect to the base 22. For example, the movement profiles can instruct the controller to move the platform at a constant rate over its length of travel, or to move the platform at a rate which varies as the table moves over its length of travel.

The table is designed such that the platform 24 can move at rates comparable to the rates at which typical tape-laying machines layup composite prepreg. Typical layup rates range from approximately 200 inches per minute to 1800 inches per minute depending upon the prepreg used and the curvature of the surface on which the tape is being placed.

Two limit switches 34 are located near either end of the base 22 of the table. The limit switches produce a signal as represented by line 36 that instructs the controller to shut down the motor 26 if the platform's length of travel exceeds the distance over which it was designed to move. This helps to ensure that the table will not be damaged if an incorrect movement profile is used in the controller.

The selection circuit 38 is connected to the controller as indicated by line 40. The selection circuit includes a thumb wheel 42 that is used to select one of the movement profiles stored in the controller. Once the desired movement profile is selected, the selection circuit 38 produces a signal which instructs the controller which movement profile to use. This results in the selection of the movement profile that corresponds to the prepreg system and tape-laying application for which tack measurements are desired as described below.

The platform 24 moves two strips of prepreg 62 into contact with a roller 54 in order to join the strips as will be discussed below. The apparatus allows the two strips of prepreg to be joined under a set of predetermined conditions, including the rate at which the strips are joined, the force applied to join the two strips, the durometer of the material from which the roller 54 is formed it and the diameter of the roller, thus allowing the apparatus to simulate the joining of a strip of prepreg to a substrate in an automatic tape playing machine.

Figure 2:
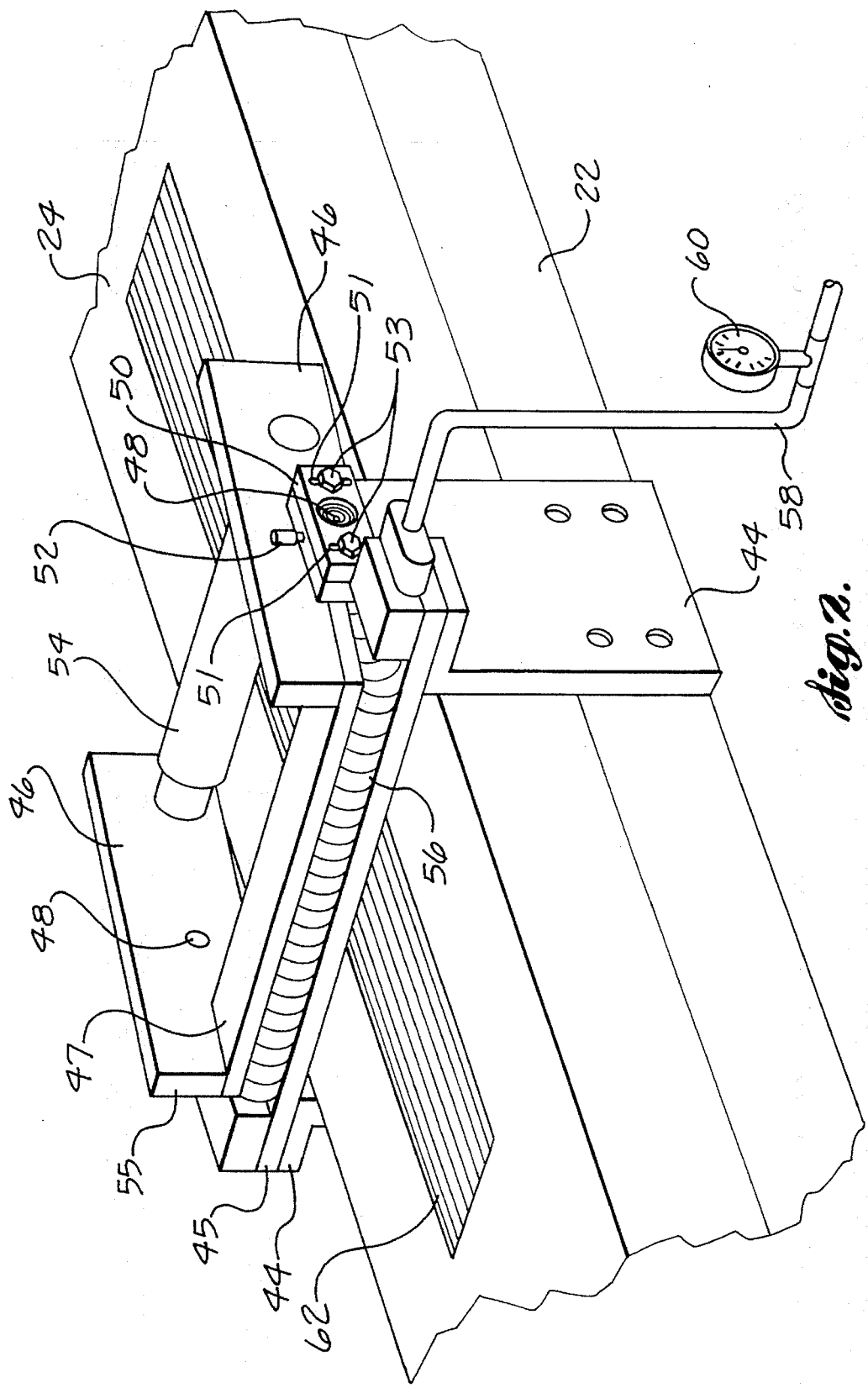
FIG. 2 is an enlarged view of the arm structure of the apparatus of FIG. 1.

As illustrated in FIG. 2, table 20 includes a frame that comprises two sides 44 that are mounted on opposing sides of table 20 and that extend upwardly above the top surface of the platform 24. A support piece 45 is attached to the upper ends of sides 44, and extends across the width of table 20 without contacting the surface of platform 24. Two adjustment plates 50 (only one of which is shown) are slidably mounted on opposite external sides of the frame through the use of two slots 51 and bolts 53. The adjustment plates can be independently moved up or down with respect to the platform 24 by loosening the bolts 53 and then rotating an adjustment screw 52.

A compaction arm formed of two side members 46, a connecting member 47, and an application roller 54 is pivotally connected to the adjustment plates 50 through the use of two pivot pins 48 (only one of which is shown). The connecting member 47 extends between the two side members 46 at one end and the application roller 54 extends between the two side members near the opposite end. As an adjustment plate 50 is independently slid up or down, the side member 46 connected to that adjustment plate also moves up or down with respect to the surface of platform 24. This allows the distance between the application roller 54 and surface of the platform to be adjusted across the width (W) of roller 54, thus allowing the roller to contact the top surface of the platform similar to how an application roller on an automated tape-laying machine could contact a curved part.

Such adjustment also allows the roller 54 to be raised away from the top surface of the platform a distance sufficient to allow a tool to be placed between the roller and the platform. This allows a piece of prepreg to be joined to the tool, as will be described below.

The application roller 54 is rotatably mounted within one end of the compaction arm 46 while the opposite end 55 including the connecting member 47 is placed in contact with a pneumatically or hydraulically inflatable actuator 56. The inflatable actuator is mounted between the frame's support piece 45 and the compaction arm's connecting member 47 such that inflation of the actuator applies an upwardly directed force to the end 55 of the compaction arm opposite the roller. This causes the compaction arm to pivot around pins 48 with respect to the base and platform 24, thus forcing the roller 54 downward into contact with the upper surface of the platform. One possible such actuator which could be used is the Merriman Windjammer available from Merriman Products, Inc., 1302 West Ganson Street, Jackson, Mich.

The actuator 56 is connected to a pressure supply (not shown) through the use of tubing 58. A combined gauge and pressure valve 60 is operatively connected within the tubing 58 such that the pressure being placed inside the actuator 56 can be adjusted. The pressure supply and actuator 56 are sized to provide a downwardly directed force to the roller 54 so that it contacts the platform with the same force used in a typical tape-laying machine. Generally, a tape-laying machine supplies a force of approximately 60–125 pounds to the application roller and thus to the prepreg being laid up.

In alternate embodiments, not shown, the inflatable actuator could be replaced by a mechanical, or electromechanical actuator. In addition, the pivotally mounted compaction arm 46 could be replaced by a device which moves vertically with respect to the platform.

In order to properly simulate the variables used in a tape-laying machine, it may be desirable to adjust the material and durometer of the material from which the application roller is formed, the diameter of the roller, the force with which the roller joins the prepreg strips, the angle at which the roller contacts the prepreg strips, and the rate at which the prepreg strips are joined, so that they correspond to the parameters used in the production automated tape-laying machine. Furthermore, it may be desirable to carry out the joining operation at the temperature and humidity present in the production facility. Properly adjusting these variables helps to ensure that the prepreg is joined, in a manner which directly corresponds to the joining achieved through the use of the tape-laying machine.

It is beneficial to determine the best layup rates and forces for joining the prepreg through experimental test runs on each different prepreg for which tack measurements are desired. This is beneficial because of the significant differences in the behavior of different prepregs, Three different variables should be experimentally determined: the average layup rate, the compaction rate, and the compaction, force. Automated tape-laying machines typically start each pass by laying up the prepreg at a slow rate to ensure that, the beginning of each strip of prepreg is properly placed and adhered to the substrate. The layup rate is subsequently increased until an average layup rate is reached. Finally, the layup rate is decreased at the end of each ply of prepreg being laid up. This decreased rate is called the tail compaction rate and it helps ensure proper compaction and adherence of the tail end of the ply of prepreg. Typically, the compaction rate is used over the last six inches of the prepreg to ensure that the end of the strip does not come free prior to curing the part. In order to work properly, the prepreg must have sufficient tack to remain adhered to the underlying substrate during the initial laydown rate, the increasing laydown rate, the average laydown rate, and the tail compaction rate.

In the preferred embodiment, a series of test runs were performed on a prepreg formed of graphite fibers embedded in a toughened epoxy resin. These tests determined that the range of force for the prepreg tested should be between approximately 60–80 pounds applied over the width of a three-inch tape. The best average layup speed for the material tested was determined to be approximately 800 inches per minute, while the best tail compaction speed was determined to be approximately 200 inches per minute. In order to accommodate production tape playing machine settings, the roller used had a diameter of 1.25 inches and was formed from a 0.25 inch thick cylinder of a 70 durometer neoprene rubber. However, these values could change depending upon the prepreg used.

In order to test the tack of a prepreg, two strips 62 of the prepreg are cut and placed on top of each other. It is desirable to place a release material between the two strips of prepreg over approximately the last 2 inches of one end in order to ensure that the strips can be separated sufficiently to mount the joined strips in the testing machine as described below. In order to ensure that the tack measurement will be representative of the production environment, it is also advantageous to precondition the prepreg at the temperature and humidity present in the production environment.

The two strips of prepreg 62 are then placed on the platform 24, and the pressure valve 60 and thumb switch 42 are adjusted in order to select the desired force and movement profile. The platform is then energized by depressing button 39 on the selection circuit (FIG. 1), causing the platform to move in accordance with the preprogrammed movement profile selected. This moves the two strips of prepreg 62 under the application roller 54, joining the two strips of prepreg along the surface between the strips.

After joining the two strips of prepreg, the joined specimen is removed from the table 20. The first test for determining whether or not a prepreg has sufficient tack is whether or not the prepreg remains adhered to the underlying substrate over the entire length of the specimen. Thus, one test of whether or not there is sufficient tack is to visually inspect the test specimen to determine whether or not the prepreg remains adhered to the underlying substrate over the portion of the specimen laid up during the acceleration portion of the laydown pass, during the constant speed portion of the laydown pass, and during the deceleration portion of the laydown pass.

Figure 3:
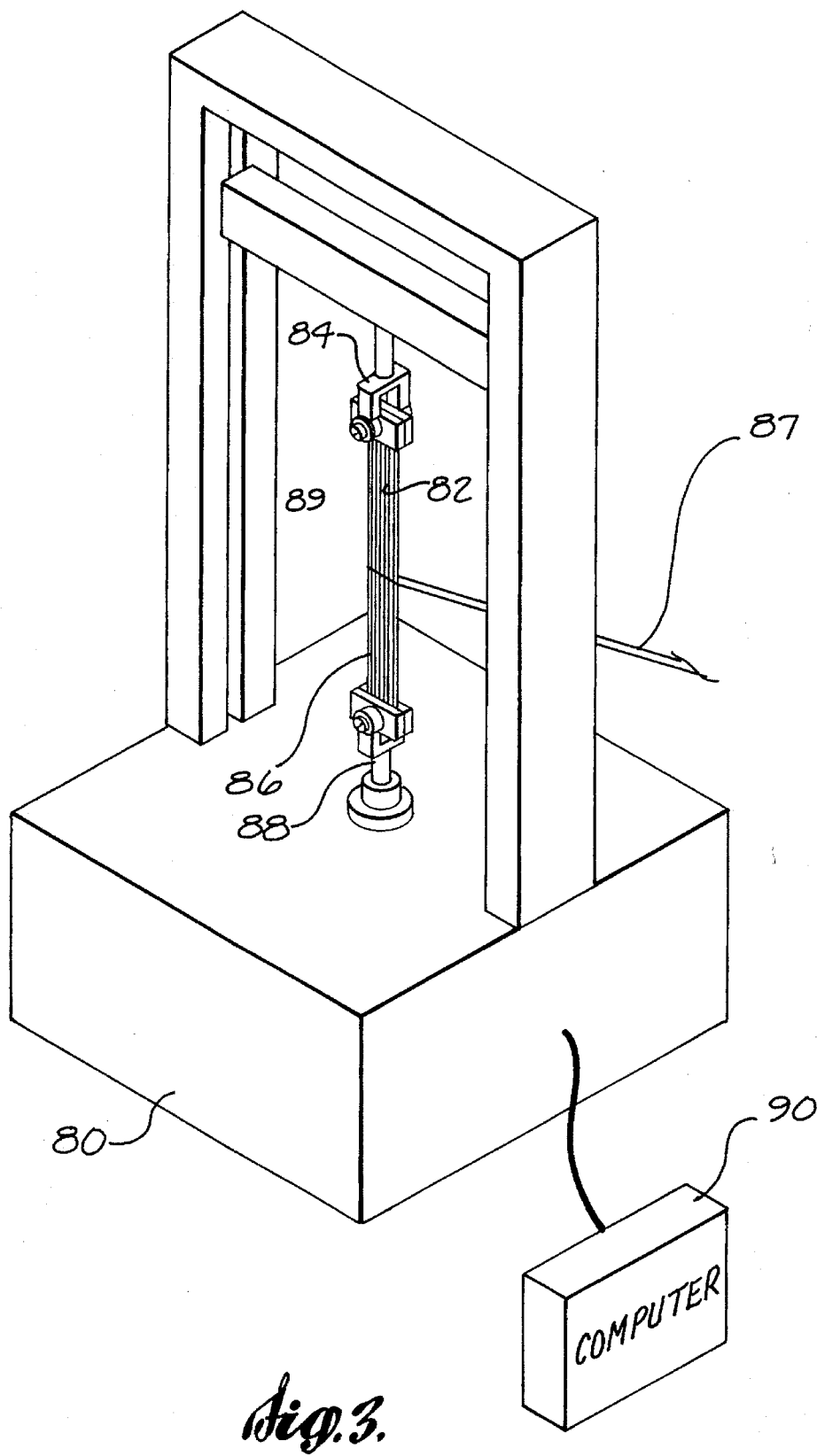
FIG. 3 is a perspective view of an embodiment of tack measurement.

After visually examining the specimen, the end of the specimen which included the release ply is separated and the specimen is placed within a standard tensile test machine 80 as illustrated in FIG. 3. In order to ensure that the exterior environment such as exposure to air over time, does not influence the test, it is advantageous to prepare and test the specimen over as small a time range as possible and in a controlled environment. A first end 82 of one of the strips of prepreg is securely clamped within a first clamp 84 while a first end 86 of the other strip is clamped within the other clamp 88. The joined portion 87 of the strips is left extending freely from the separated portion of the first and second strips. The two strips of prepreg are then peeled apart through the use of the tensile test machine. The tensile test machine moves the clamp 84 vertically away from the clamp 88 such that the two strips of prepreg are peeled apart along the joining surface 89 at approximately 180 degrees to each other.

In alternate embodiments (not shown) a different test set-up could be used to separate the two strips of joined prepreg. It is important that the ends of the two strips be separated in a direction at least partially normal to the joined surface, but they do not have to be separated at 180 degrees to each other. As an example, one side of the joined strips could be attached to a flat plate and one end of the strip not attached to the plate could be separated from the plate, at for example, 90 degrees to the plate. However, it is believed that the best results are obtained by separating the ends of the strips at approximately 180 degrees to each other.

While the strips of prepreg are being separated, a recorder or computer 90 records the force and displacement used to separate the two strips of prepreg. During the testing, it is advantageous to operate the test machine in stroke control, where the machine peels the two strips of prepreg apart at a constant rate of displacement. Operating the machine in stroke control allows the force to vary as the two pieces of prepreg are peeled apart. In order to ensure proper test results, it is desirable to perform experimental tests on each different prepreg to ensure that a proper displacement rate is used during testing. The displacement rate that produces the most consistent values of tack should be used. For prepreg formed of graphite fibers and a toughened epoxy matter used, in the test runs, the separation rate had little effect upon the test data. Therefore, a high rate of separation of approximately five inches per minute is used in order to minimize the amount of time necessary to perform the test. Each time a new prepreg is tested, however, it may he beneficial to perform a series of tests in order to ensure that the separation rate has minimal effect upon the test results.

Figure 4:
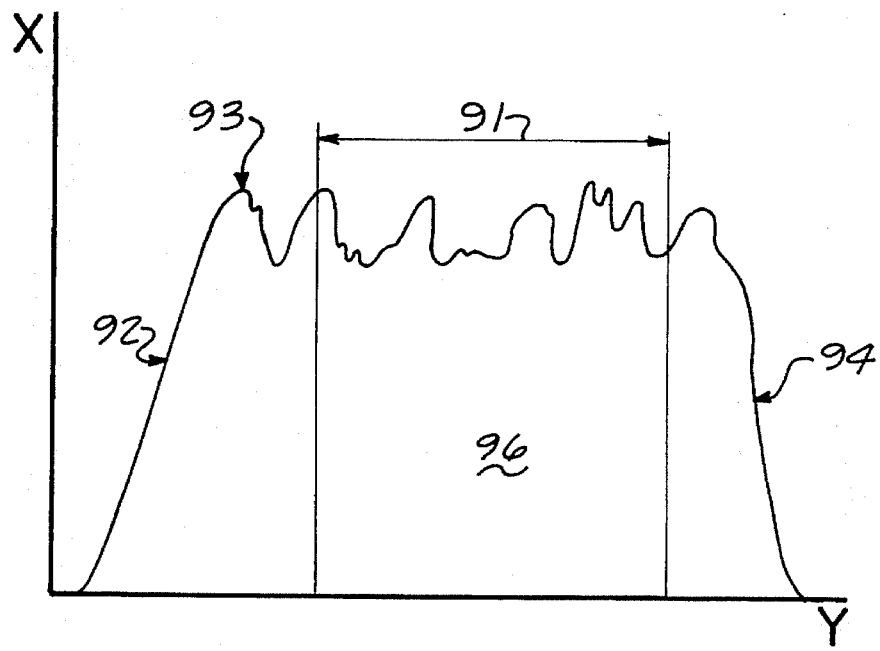
FIG. 4 is a graph of the data recorded for an example of tack measurement, wherein displacement is plotted along the x-axis and force is plotted along the y-axis.

FIG. 4 illustrates a typical plot of the load versus displacement data obtained from a specimen joined at a constant rate over the length of the specimen. Displacement is plotted along the x-axis while the force measured during the test is plotted along the y-axis. As shown by the rising edge 92, the force slowly increases as the test begins until the peak 93 of the rising edge is reached. The force then fluctuates around an average value until the force decreases at the end of the test as shown by the declining edge 94.

Two preferred quantities used as measurements of tack are the average force and energy used to separate the two strips of prepreg during the peel test. In order to ensure that inaccuracies are not introduced into the test due to the loading or unloading of the specimen, it is desirable to determine the average force over the lead versus displacement plot after force stabilization has occurred. Therefore, the average force is determined over a displacement range 91 selected such that the peak 93 of the rising edge has been reached and the declining edge 94 has not been reached. The exact boundaries of the range 91 are not critical as long as it is determined as indicated above. In the preferred embodiment, the computer 90 (FIG. 3) averages the measured force over the range 91 and then divides this average by the width of the specimen to indicate a value of tack as an average force per unit width, such as lbs/in.

According to the present invention, the energy under the lead versus displacement curve can also be used as a value of tack. As illustrated in FIG. 4, the energy is the area 96 under the lead versus displacement curve within the test range 91. The area 96 is calculated by integrating the area under the lead versus displacement curve through the use of the computer 90, producing a measurement of tack as total force times a displacement, such as lbs/in.

Both the energy under the lead versus displacement curve and the average force per unit width are good representative values of tack. However, the use of the energy under the load versus displacement curve could have a number of advantages. Experimental tests have shown that the rate at which the prepreg is joined affects the value of tack measured. Therefore, if a movement profile whose rate varies over the length of the strips are used, the resulting load versus displacement curve differs from the curve shown in FIG. 4.

Figure 5:
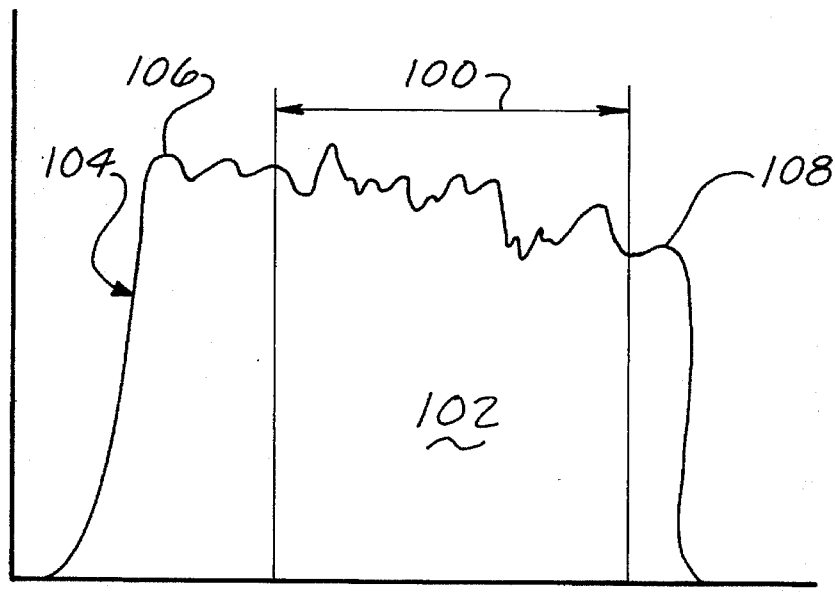
FIG. 5 is a graph of the data recorded for a second example of tack measurement, wherein displacement is plotted along the x-axis and force is plotted along the y-axis.

FIG. 5 shows a typical load versus displacement curve which results if the strips are joined through the use of a movement profile whose rate increases over the length of the strips. As shown, during testing, an average force 106 measured at the beginning of the strips where the layup rate was slower is higher than an average force 108 measured at the end of the strips where the layup rate was faster. In the example shown, if a tack measurement is taken over the range 100, the energy 102 under the load versus displacement curve 104 could take into account the varying layup rate used to join the specimen. This type of measurement could be more beneficial than an average force measurement in accounting for varying layup rates used on tape-laying machines.

Figure 7:
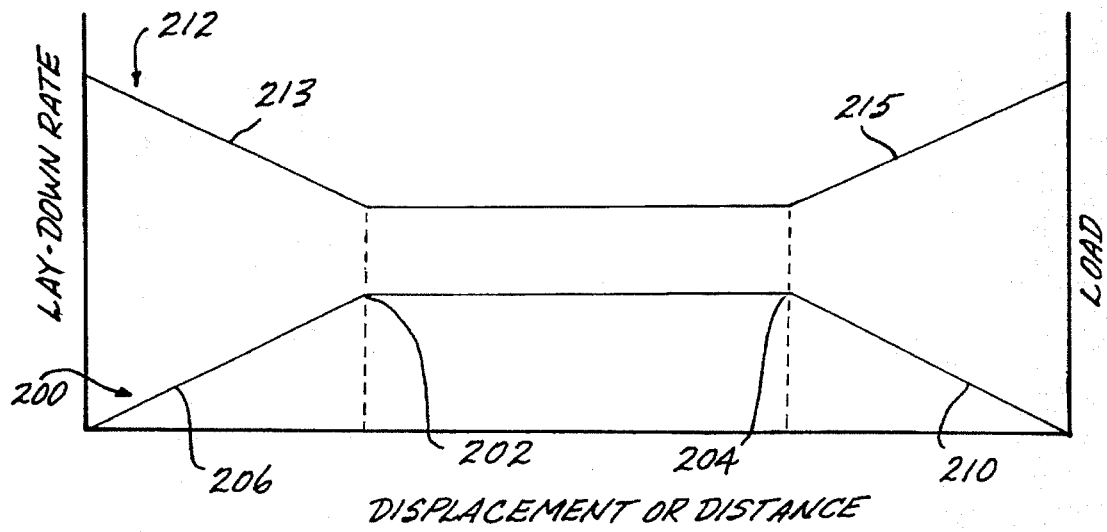
FIG. 7 is a graph of a simulated layup rate profile and resulting load versus displacement profile necessary to separate two pieces of prepreg, wherein displacement and distance are plotted along the x-axis, and load and laydown rate are plotted along the y-axis.

FIG. 7 shows a typical load versus displacement curve and laydown rate versus distance over the length of the specimen curve for a specimen joined with a laydown rate profile used in a representative tape-laying machine. As discussed above, over a single laydown pass, the speed of the tape-laying machine will start out slow, increase steadily until a constant laydown rate is reached, maintain a constant laydown rate, and then decrease speed at the tail compaction portion of each laydown pass. This laydown rate profile is illustrated in FIG. 7 by curve 200 which is a plot of laydown rate versus the distance that the compaction roller has made contact with the specimen, i.e., the distance along the length of the test specimen. The laydown or joining rate increases steadily as shown by upward sloped ramp 206 until a maximum rate is achieved at point 202. The laydown rate is then maintained constant until the laydown rate is decreased starting at point 204 for tail compaction, as shown by downward sloped ramp 210. The slope of the ramp 206 and 210 are selected to simulate the actual performance expected by the tape-laying machine during production.

Curve 212 in FIG. 7 is a representative load versus displacement curve for a test specimen joined through the use of the movement profile illustrated by curve 200. As shown by a curve 212, the load necessary to separate the strips of prepreg decreases as shown by downward sloped ramp 213 as the rate at which the strips are joined increases, remains relatively constant as the rate at which the strips are joined remains constant, and increases along ramp 215 as the rate at which the strips are joined decreases.

After joining two strips of prepreg as described above, a visual inspection may be performed on the joined strips to determine whether or not they adhered over the entire length of the specimen. The specimen may then be tested as described above and the resulting load versus displacement history compared to an acceptable load versus displacement history to determine whether or not the tack is sufficient. If the value of the measured load per unit area is below an experimentally determined threshold value in either the increasing laydown rate portion, constant laydown rate portion, or decreasing laydown rate portion of the specimen, the batch of prepreg may be found unacceptable.

In practice, layup conditions for the prepreg, including the layup rate, layup force, durometer of material used to form the roller, and the diameter of the roller, could be determined through test runs on an automated tape-laying machine using a first batch of prepreg. The layup conditions could be determined experimentally by changing the conditions until good adhesion between the prepreg tape and the part or substrate on which the prepreg is being laid up is achieved. These conditions could then be used to set up the joining apparatus. Strips of the first batch of prepreg would then be joined with the joining apparatus and a reference value of tack would be determined as described above. This reference value of tack would then be used to determine whether other batches of prepreg have acceptable tack. Each new batch of prepreg arriving at the production facility could be tested as described above. If the value of tack measured for the new batch of prepreg is the same as or within an acceptable range of the reference value of tack, the batch is accepted for use on the automated tape-laying machine. Otherwise it is rejected, thus helping to ensure quality control of the prepreg prior to use in the tape-laying machine.

Alternatively, the method and apparatus of the present invention could be used to determine a value of tack for prepreg subject to joining under a predetermined set of conditions. This could be very helpful during the development of new prepreg. In this embodiment, a general set of joining conditions are determined and two strips of each new batch of prepreg are joined using these conditions and tested as described above to determine a value of tack. The prepreg developer can use the value of tack to monitor whether and to what extent changes in the prepreg's fabrication process produce changes in the prepreg's tack. It may be beneficial to use joining conditions commonly used for the application for which the new prepreg is intended. Additionally, a user could supply a prepreg developer with the joining conditions and a desired value of tack. The developer could then change the fabrication process until a prepreg with the desired value of tack is produced.

In yet another embodiment of the present invention, a strip of prepreg could be joined to a tool using the joining apparatus described above and then separated from the tool as described below in order to determine the ability of the prepreg to adhere to the tool. In a production environment, the tool upon which the prepreg is to be laid up is first coated with a release agent which allows the part to be separated from the tool after curing. The release agent influences the ability of the prepreg to adhere to the tool upon which the prepreg is being laid up. In order to increase the prepreg's adherence to the tool, it is often beneficial to spray a coat of epoxy resin over the top of the release coat prior to laying up the first ply of prepreg.

The method and apparatus of the present invention can be used to determine whether a prepreg has sufficient tack to adhere to the release coated or epoxy coated tool. In this embodiment, the roller 54 is raised as described above, and a flat tool is placed between the roller and the top surface of the platform. The tool could be coated with the release coat and resin coat used in the production environment. A strip of prepreg is then placed on top of the tool and joined to the tool as described above. If upon joining, the strip of prepreg fails to adhere to the tool and instead one end or all of the strip lifts away from the tool, the combination of prepreg, release coat and coat of resin is unworkable. However, if the strip of prepreg visually adheres to the tool the tack of the prepreg could be measured as described below.

Figure 6:
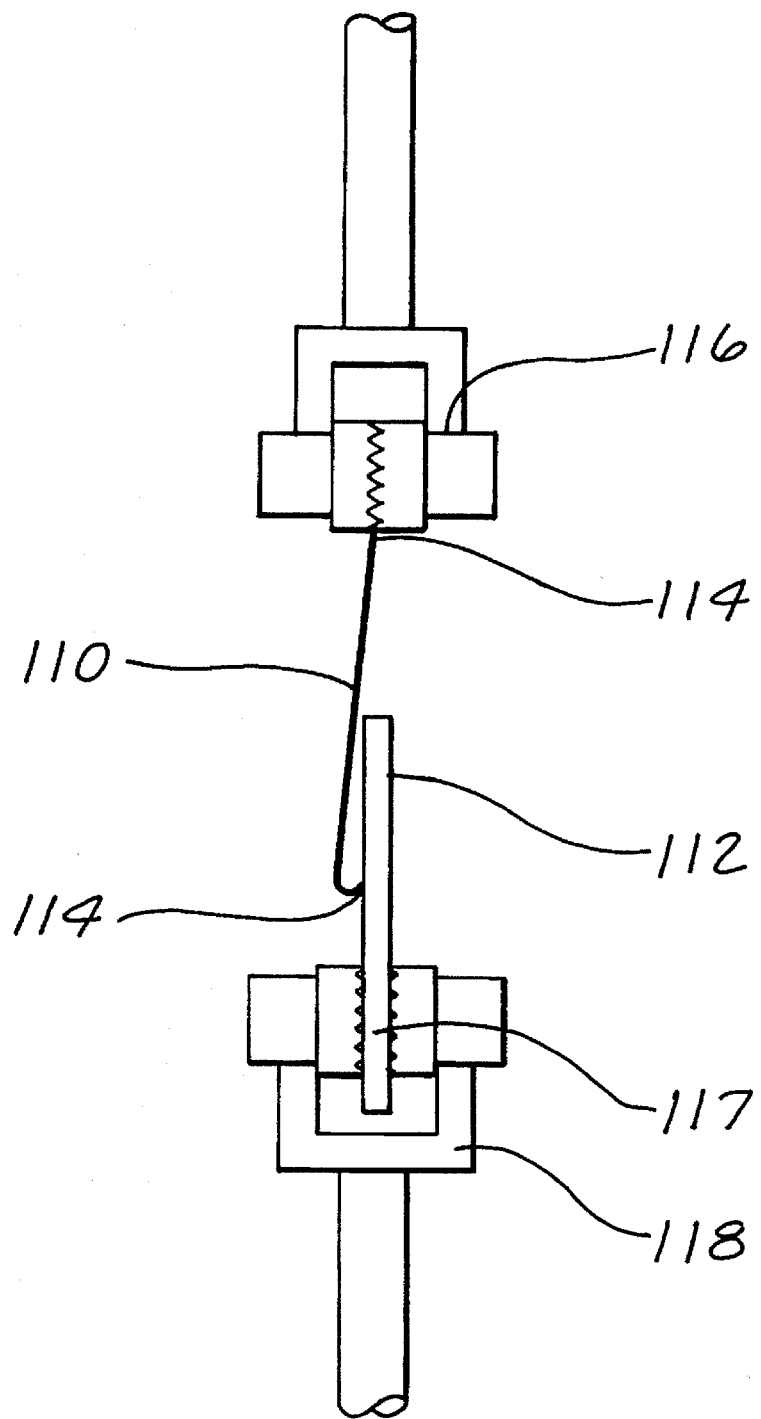
FIG. 6 is a partial side elevational view of a second embodiment of tack measurement.

FIG. 6 illustrates an embodiment of a test set up to separate a strip of prepreg 110 from a tool 112 to which it has been joined as described above. One end 114 of the strip is separated from the tool 112 and secured within a clamp 116 of a tensile test machine. One end 117 of the tool is secured in the other clamp 118 of the test machine. The tensile test machine is then operated in stroke control as described previously in order to separate the strip 110 from the tool 112. As shown in FIG. 6, the strip is separated from the tool in a direction 180 degrees from the joined surface 114 in between the strip and the tool.

While separating the strip of prepreg from the tool, the separation force is measured and a value of tack is determined as described previously. The measured value of tack is then compared to the reference value of tack, which has been experimentally determined as described above. If the measured value of tack is within a tolerance range of the reference value of tack, the combination of prepreg, release coat, and coat of resin produces a sufficient degree of adherence in between the prepreg and the tool. If the measured value of tack is not within a tolerance range of the reference value of tack, a new release coat, resin coat, or prepreg material can be substituted and the procedure described above repeated until an acceptable measurement of tack results.

Figure 8:
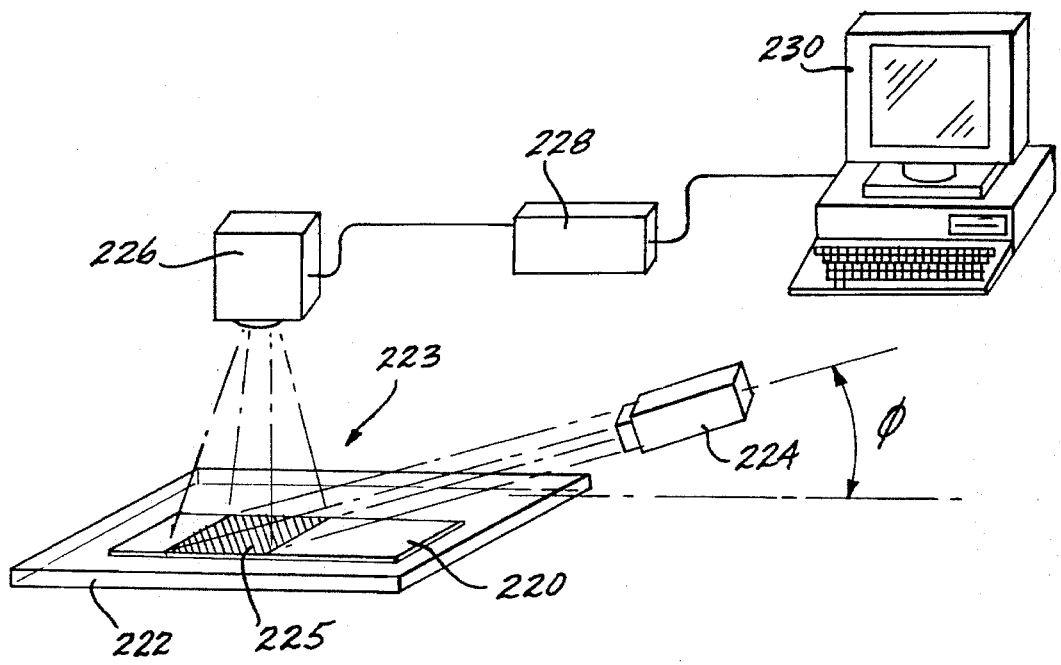
FIG. 8 is a schematic representation of an alternate method and apparatus of tack measurement using a contrast analyzer in accordance with the present invention.

FIG. 8 illustrates an alternate embodiment of the present invention for determining whether or not a batch of prepreg has sufficient tack. The alternate embodiment uses contrast analysis to determine a percent adhesive contact area between a strip of prepreg and a visually transparent substrate. The measurement of percent adhesive contact area is then used as a measurement of tack.

In the alternate embodiment as illustrated in FIG. 8, a strip of prepreg 220 is joined to a visually transparent substrate 222 to form a test specimen 223 in a manner similar to that described with respect to the first embodiment. The visually transparent substrate 222 could be a sheet of glass, frosted glass, acrylic, polycarbonate, or other visually transparent material. After joining, the test specimen 223 is oriented such that the strip of prepreg is underneath the visually transparent substrate so that the adhesive interface between the strip of prepreg and transparent substrate is viewable. A contrast analyzer is then used to determine the percent adhesive contact area between the strip of prepreg and the substrate as described in detail below.

The test specimen 223 is placed in a black room and the area 225 of the specimen to be analyzed is illuminated through the use of a light source 224. The angle of incidence φ of the light source is adjusted in order to get the best illumination of the specimen. In the alternate embodiment, the best angle of incidence φ has been determined to be approximately 25° from the plane of the specimen. Performing the contrast analysis in a dark room and using an incident light source as described above helps to reduce the effect of ambient light on the contrast analysis.

The area 225 of the specimen illuminated by the light source is located underneath a video camera 226 mounted perpendicular to the test specimen. The video camera 226 acquires an image of the adhesive contact area between the strip of prepreg and the transparent substrate. This image is then converted into a digital format through the use of a video grabber 228 attached to the camera. The video grabber in turn passes the digitized image to a computer 230 that performs a contrast analysis as described below.

Figure 9:
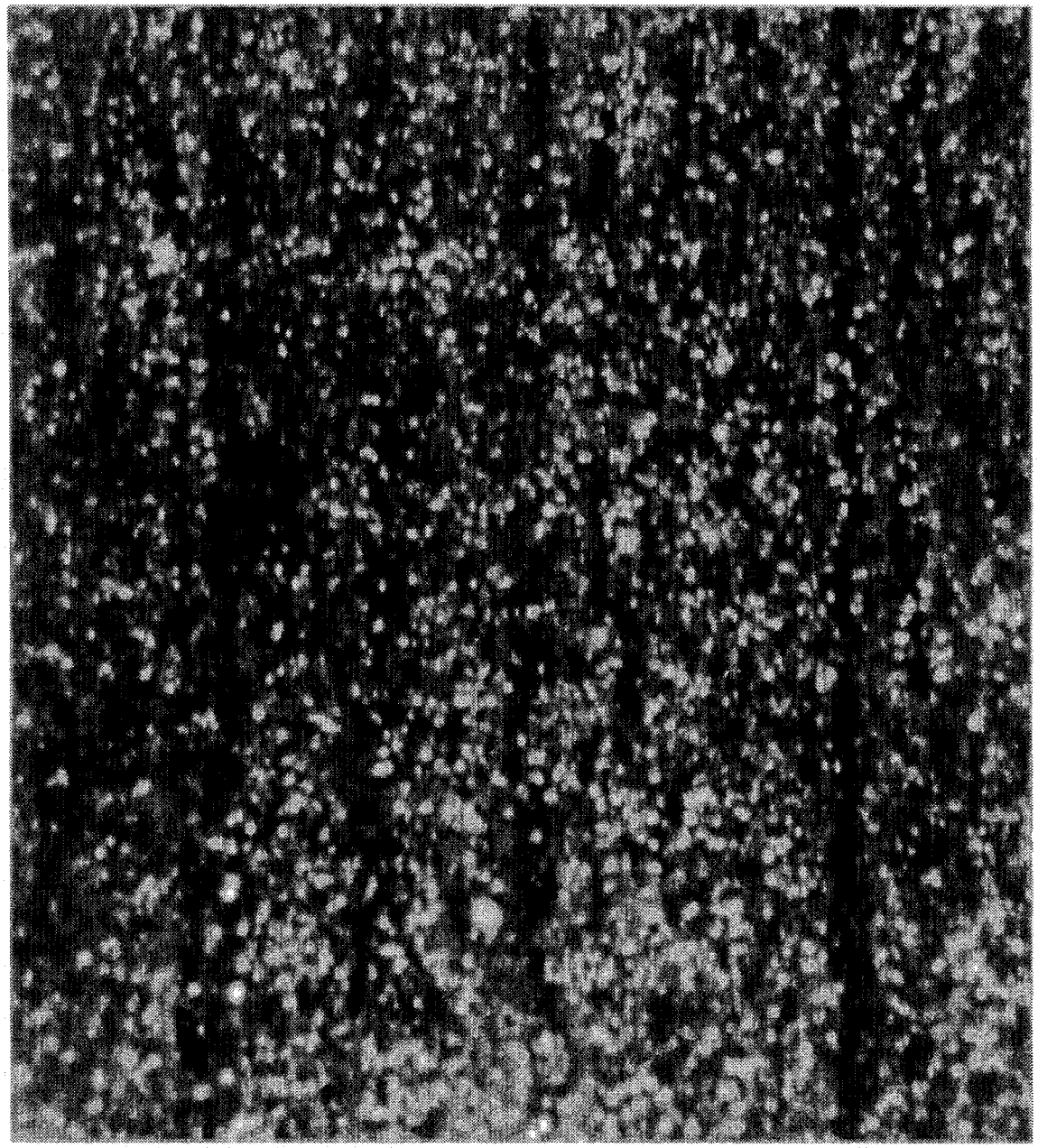
FIG. 9 is a representative photograph produced by the contrast analyzer of FIG. 8 illustrating the adherence between the prepreg and a visually transparent substrate.

FIG. 9 illustrates a typical image of the adhesive contact area produced by camera 226. In the image, the adhesive contact area between the prepreg strip and the underlying substrate is shown by the contrasting gray scale of the image. The areas of best adhesive contact between the prepreg and the underlying substrate are of the darkest color or contrast while the areas of less adhesive contact are of lighter colors or contrasts. Thus, the darker the gray scale the better the adhesive contact between the prepreg strip and the substrate.

The image produced by the camera 226 is digitized by the video grabber 228. The video grabber 228 could be any suitable device capable of digitizing the image produced by the camera 226. In the alternate embodiment, a Matrox™ MVP-AT video grabber capable of producing 512×480 pixel resolution images is used.

After digitization, the image is passed to the computer 230 for analysis. The computer uses suitable image analysis software to determine the number or count of pixels having a certain contrast or gray scale. The computer then uses the pixel count to determine a threshold gray scale or contrast value as described below. Using the threshold value, the computer sums up the number or count of pixels having a gray scale or contrast as dark or darker than the threshold value. The sum of pixels having a contrast darker than the threshold value is then divided by the total number of pixels in the image to determine the percent adhesive contact area between the strip of prepreg and the underlying substrate. The value of percent adhesive contact area is used as a measurement of prepreg tack. If the measurement of percent adhesive contact area is greater than a previously determined acceptable percent adhesive contact area, the prepreg has an acceptable level of tack, otherwise it does not.

Figure 11:
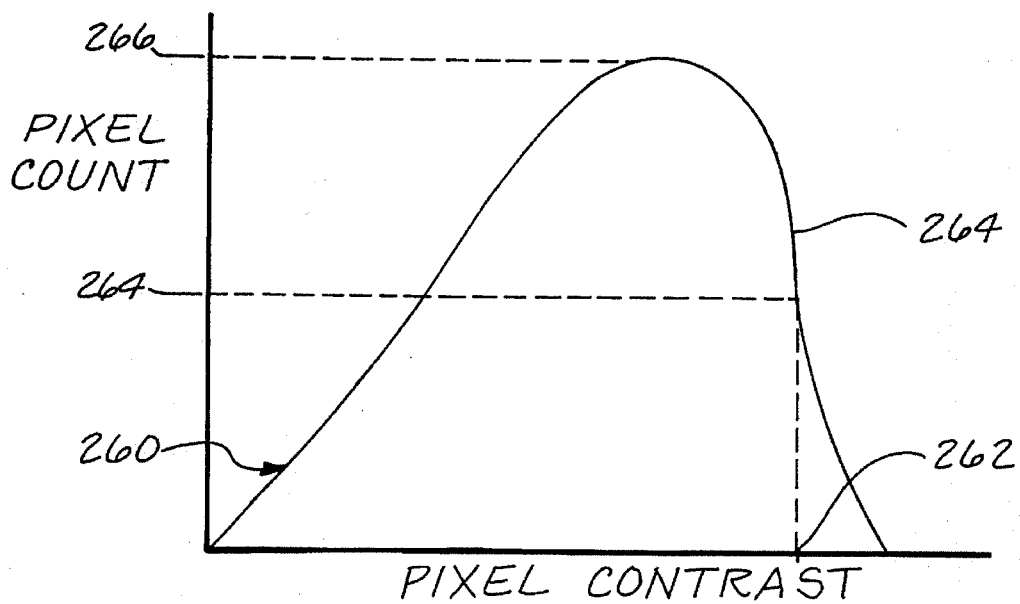
FIG. 11 is a graph of an alternate method of determining a threshold contrast value for use in the present invention, wherein pixel contrast is plotted along the x-axis and pixel count is plotted along the y-axis.
Figure 10:
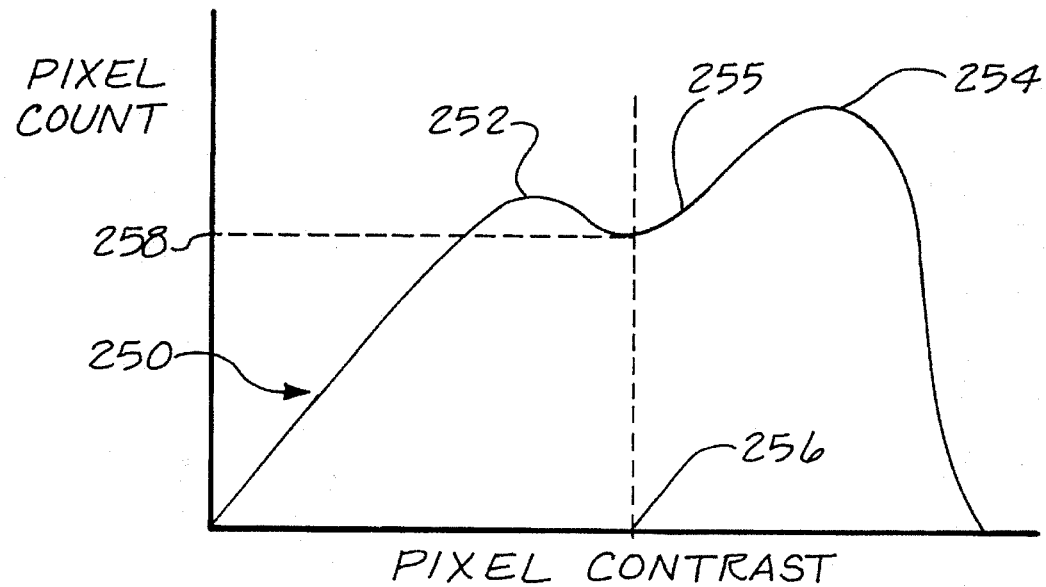
FIG. 10 is a graph of a method of determining a threshold contrast value for use in the present invention, wherein pixel contrast is plotted along the x-axis and pixel count is plotted along the y-axis.

FIGS. 10 and 11 illustrate two different methods to determine a threshold contrast value in accordance with the present invention. In the method illustrated in FIG. 10, the computer determines the pixel count, i.e., the sum of pixels, at a certain color or contrast and plots the resulting data on a graph having pixel contrast represented along the x-axis and pixel count represented along the y-axis. Experimental analysis has shown that in some combinations of substrate and prepreg the graph of pixel contrast versus pixel count will form a curve 250 having a binodal distribution with two nodes or peaks 252 and 254 and a valley 255. When binodal behavior is present, the threshold contrast value is determined as the value of pixel contrast 256 at which the minimum pixel count 258 between the two peaks 252 and 254 occurs.

In prepreg substrate combinations that do not have a binodal behavior, pixel contrast is plotted versus pixel count as represented by curve 260 of FIG. 11. The threshold contrast value 262 is then determined as the value of pixel contrast along the declining edge 264 of curve 260 at a value of pixel count 262 that is one-half of the peak value of pixel count 266.

For illustrative purposes only, in the alternate embodiment, a Nikon 55 millimeter video camera having a 300 meter lens was used. The camera was located ten inches perpendicularly above the test specimen. A Matrox™ MVP-AT frame grabber was used to create a digital image having a 512×480 pixel array. Image Pro™ software was then used to determine the pixel count and pixel contrast. The data produced by the software was then used to determine a threshold contrast value and a value of percent contact area.

While the preferred embodiment of the invention has been illustrated and described, it will be appreciated that various changes can be made therein without departing from the spirit and scope of the invention. Although the joining apparatus and tack measurements of the present invention have been discussed in relation to automated tape-laying machines, they are also applicable for use in the quality control of prepreg used in hand layup operations.

The embodiments of the invention in which an exclusive property or privilege is claimed are defined as follows:

1. A method for establishing whether the tack of a composite prepreg is within an appropriate range to adhere to a substrate when joined to the substrate under predetermined condition, the method comprising the step of:
   (a) joining a strip of a first batch of prepreg to a substrate that is least partially visually transparent under the predetermined conditions;
   (b) producing a digital image of an adhesive contact area between the strip of prepreg and the substrate;
   (c) using the digital image, producing a representation of the digital image as a function of pixel count of pixel contrast, and determining whether the representation of the digital image has binodal behavior;
   (d) when the representation of the digital image has binodal behavior, determining a threshold contrast value as the value of contrast at a lowest value of pixel count between two peak values of pixel count;
   (e) using the digital image, summing a number of pixels in the image having a contrast greater than the threshold contrast value and determining a measurement of percent adhesive contact area between the strip of prepreg and the substrate using the sum of the number of pixels;
   (f) repeating steps (a) through (d) for a second batch of prepreg to produce a measurement of precent adhesive contact area for the second batch of prepreg; and
   (g) comprising the measurement of precent adhesive contact area for the second batch of prepreg with the measurement of percent adhesive contact area for the first batch of prepreg, thereby determining whether the tack of the second batch of prepreg is within the appropriate range.

2. The method of claim 1, further comprising the step of when the representation of the digital image does not have binodal behavior determining the threshold contrast value as pixel contrast value a value of pixel count that is one-half a maximum value of pixel count.

3. The method claim 1, wherein the predetermined conditions include a rate at which the strip of prepreg is joined to the substrate and wherein the joining step further comprises joining the strip of prepreg to the substrate at a rate which varies over the length of the strip.

4. The method of claim 3, wherein the joining step further comprises joining the strip of prepreg to the substrate at a rate which increase over a first portion of the strip and decreases over a second portion of the strip.

5. An apparatus for determining whether the tack of a composite prepreg is within an appropriate range to adhere to a substrate when joined to the substrate under predetermined conditions, the apparatus comprising:
   means for joining a strip of prepreg to a substrate that is at least partially visually transparent along a contact surface, and
   measurement means for determining a measurement of percent adhesive contact area between the strip of prepreg and the substrate along the contact surface, the measurement means including means for producing a digital image of the contact surface, means for producing a representation of the digital image as a function of pixel contrast, means for determining whether the representation of the digital image has binodal behavior, means for determining a threshold contrast value as the value of contrast at a lower value of pixel count between two peak values of pixel count when the representation of the digital image has binodal behavior, and means for summing a number of pixels in the image having a contrast greater than the threshold contrast value.

6. The apparatus of claim 5, wherein the means of joining the strip of prepreg further comprises means for joining the strip of prepreg to the substrate at a rate which varies over the length of strip of prepreg.

7. The apparatus of claim 5, wherein the measurement means includes means for determining the threshold contrast value as a pixel contrast value at a value of pixel count that is one-half a maximum value of pixel count when the representation of the digital image does not have binodal behavior.

* * * * *

UNITED STATES PATENT AND TRADEMARK OFFICE
CERTIFICATE OF CORRECTION

PATENT NO. : 5,513,537  Page 1 of 2
DATED : May 7, 1996
INVENTOR(S) : J.R. Brooks et al.

It is certified that error appears in the above-indentified patent and that said Letters Patent is hereby corrected as shown below:

COLUMN     LINE

13             27            "condition, the method comprising the step" should
(Claim 1,  line 4)           read --conditions, the method comprising the steps--

13             29            "is least" should read --is at least--
(Claim 1,  line 6)

13             35            "count of" should read --count and--
(Claim 1,  line 11)

13             49            "precent" should read --percent--
(Claim 1,  line 25)

13             51            "comprising the measurement of precent" should
(Claim 1,  line 27)          read --comparing the measurement of percent--

14             7             "pixel contrast value a" should read --a pixel
(Claim 2,  line 4)           contrast value at a--

14             16            "increase" should read --increases--
(Claim 4,  line 3)

14             25            "surface," should read --surface;--
(Claim 5,  line 7)

UNITED STATES PATENT AND TRADEMARK OFFICE
CERTIFICATE OF CORRECTION

PATENT NO.   : 5,513,537
DATED        : May 7, 1996
INVENTOR(S)  : J.R. Brooks et al.

It is certified that error appears in the above-indentified patent and that said Letters Patent is hereby corrected as shown below:

| COLUMN | LINE | |
|---|---|---|
| 14 (Claim 5, | 33 line 14) | "pixel contrast," should read --pixel count and pixel contrast,-- |
| 14 (Claim 5, | 36 line 17) | "lower" should read --lowest-- |
| 14 (Claim 6, | 42 line 1) | "of joining" should read --for joining-- |
| 14 (Claim 6, | 45 line 4) | "of strip" should read --of the strip-- |

Signed and Sealed this

Fifteenth Day of October, 1996

Attest:

BRUCE LEHMAN

*Attesting Officer*       *Commissioner of Patents and Trademarks*